(12) United States Patent
Racila et al.

(10) Patent No.: US 7,723,036 B2
(45) Date of Patent: May 25, 2010

(54) ASSESSING RESPONSE TO ANTI-CD20 THERAPY BY GENOTYPING C1Q COMPONENTS

(75) Inventors: Emilian V. Racila, North Liberty, IA (US); George J. Weiner, Iowa City, IA (US)

(73) Assignee: The University of Iowa Research Foundation, Iowa City, IA (US)

(*) Notice: Subject to any disclaimer, the term of this patent is extended or adjusted under 35 U.S.C. 154(b) by 237 days.

(21) Appl. No.: 11/505,635

(22) Filed: Aug. 17, 2006

(65) Prior Publication Data
US 2007/0128626 A1    Jun. 7, 2007

Related U.S. Application Data

(60) Provisional application No. 60/709,393, filed on Aug. 18, 2005.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search ................ None
See application file for complete search history.

(56) References Cited

OTHER PUBLICATIONS

Juppner H. Bone (Aug. 1995) vol. 17, No. 2, Supplement pp. 39S-42S.*
Farag S.S. et al. Blood (Feb. 2004) vol. 103, No. 4, pp. 1472-1474.*
Thisted R.A. 'What is a P-value?' (May 25, 1998), available from http://www.stat.uchicago.edu/~thisted, pp. 1-6.*
Racila E. et al. 'A Polymorphism in the C1qA Component of Complement Correlates with Prolonged Complete Remission Following Rituximab Therapy of Follicular Lymphoma.' Blood (ASH Annual Meeting Abstracts) 2005 106: Abstract 778.*
Galimberti S. et al. Journal of Chemotherapy (2007) vol. 19, No. 3, pp. 315-321.*
Weng W.-K. et al. 'Two Immunoglobulin G Fragment C Receptor Polymorphisms Independently Predict Response to Rituximab in Patients With Follicular Lymphoma' J Clin Oncol (2003) 21:3940-3947.*
Racila E. et al. A Polymorphismin the Complement Component C1qA Correlates with Prolonged Response Following Rituximab Therapy of Follicular Lymphoma Clin Cancer Res 2008; 14(20), pp. 6697-6703.*
Di Gaetano et al., "Complement activation determines the therapeutic activity of rituximab in vivo," *J. Immunol.*, 171:1581-1587, 2003.
Hacker et al., "Lack of association between an interleukin-1 receptor antagonist gene polymorphism and ulcerative colitis," *Gut*, 40:623-627, 1997.
PCT International Search Report and Written Opinion, issued in International Application No. PCT/US06/32173, dated Jan. 17, 2008.
Shi et al., "Trends in therapeutic monoclonal antibodies of cancer," *Expert Opin. Ther. Patents*, 17:1047-1059, 2005.
Witzig et al., "Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma," *J. Clin. Oncol.*, 20:2453-2463, 2002.
Demidem et al., "Chimeric anti-CD20 (IDEC-C2B8) monoclonal antibody sensitizes a B cell lymphoma cell line to cell killing by cytotoxic drugs," *Cancer Biother. Radiopharm.*, 12(3):177-186, 1997.
Donin et al., "Complement resistance of human carcinoma cells depends on membrane regulatory proteins, protein kinases and sialic acid," *Clin. Exp. Immunol.*, 131(2):254-263, 2003.
Duan et al., "Synonymous mutations in the human dopamine receptor D2 (DRD2) affect mRNA stability and synthesis of the receptor," *Hum. Mol. Genet.*, 12(3):205-216, 2003.
Fishelson et al., "Obstacles to cancer immunotherapy: expression of membrane complement regulatory proteins (mCRPs) in tumors," *Mol. Immunol.*, 40(2-4):109-123, 2003.
Gelderman et al., "Complement function in mAb-mediated cancer immunotherapy," *Trends Immunol.*, 25(3):158-164, 2004.
Gorter and Meri, "Immune evasion of tumor cells using membrane-bound complement regulatory proteins," *Immunol. Today*, 20(12):576-582, 1999.
Racila et al., "Homozygous single nucleotide polymorphism of the complement C1QA gene is associated with decreased levels of C1q in patients with subacute cutaneous lupus erythematosus," *Lupus*, 12(2):124-132, 2003.
Reff et al., "Depletion of B cells in vivo by a chimeric mouse human monoclonal antibody to CD20," *Blood*, 83(2):435-445, 1994.

* cited by examiner

*Primary Examiner*—Stephen Kapushoc
(74) *Attorney, Agent, or Firm*—Fulbright & Jaworski

(57) ABSTRACT

The present invention encompasses methods for predicting metastasis in cancer by assessing the structure of the complement protein C1qA. The methods may encompass examining either protein or nucleic acids, and may further include making treatment decisions based on the predictive methods.

12 Claims, 2 Drawing Sheets

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
tgagtgtgtg aagatgtggg                                                    20

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
agggtagtgg ttaaacacag g                                                  21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 3
taaaggagac caggggggaac                                                   20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:  Synthetic
      Primer
```

<400> SEQUENCE: 4
ttgaggagga gacgatggac                                                    20

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
gagtctcatg gaatcac                                                       17

<210> SEQ ID NO 6
<211> LENGTH: 955
<212> TYPE: DNA
<213> ORGANISM: Artificial Sequence
<220> FEATURE:
<223> OTHER INFORMATION: Description of Artificial Sequence: Synthetic
      Primer
<220> FEATURE:
<221> NAME/KEY: CDS
<222> LOCATION: (1)..(735)

<400> SEQUENCE: 6

```
atg gag ggt ccc cgg gga tgg ctg gtg ctc tgt gtg ctg gcc ata tcg        48
Met Glu Gly Pro Arg Gly Trp Leu Val Leu Cys Val Leu Ala Ile Ser
 1               5                  10                  15 ctg gcc tct atg gtg acc gag gac ttg tgc cga gca cca gac ggg aag        96
Leu Ala Ser Met Val Thr Glu Asp Leu Cys Arg Ala Pro Asp Gly Lys
             20                  25                  30 aaa ggg gag gca gga aga cct ggc aga cgg ggg cgg cca ggc ctc aag       144
Lys Gly Glu Ala Gly Arg Pro Gly Arg Arg Gly Arg Pro Gly Leu Lys
         35                  40                  45 ggg gag caa ggg gag ccg ggg gcc cct ggc atc cgg aca ggc atc caa       192
Gly Glu Gln Gly Glu Pro Gly Ala Pro Gly Ile Arg Thr Gly Ile Gln
     50                  55                  60 ggc ctt aaa gga gac cag ggg gaa cct ggg ccc tct gga aac ccc ggc       240
Gly Leu Lys Gly Asp Gln Gly Glu Pro Gly Pro Ser Gly Asn Pro Gly
 65                  70                  75                  80 aag gtg ggc tac cca ggg ccc agc ggc ccc ctc ggg gcc cgt ggc atc       288
Lys Val Gly Tyr Pro Gly Pro Ser Gly Pro Leu Gly Ala Arg Gly Ile
                 85                  90                  95 ccg gga att aaa ggc acc aag ggc agc cca gga aac atc aag gac cag       336
Pro Gly Ile Lys Gly Thr Lys Gly Ser Pro Gly Asn Ile Lys Asp Gln
            100                 105                 110 ccg agg cca gcc ttc tcc gcc att cgg cgg aac ccc cca atg ggg ggc       384
Pro Arg Pro Ala Phe Ser Ala Ile Arg Arg Asn Pro Pro Met Gly Gly
        115                 120                 125 aac gtg gtc atc ttc gac acg gtc atc acc aac cag gaa gaa ccg tac       432
Asn Val Val Ile Phe Asp Thr Val Ile Thr Asn Gln Glu Glu Pro Tyr
    130                 135                 140 cag aac cac tcc ggc cga ttc gtc tgc act gta ccc ggc tac tac tac       480
Gln Asn His Ser Gly Arg Phe Val Cys Thr Val Pro Gly Tyr Tyr Tyr
145                 150                 155                 160 ttc acc ttc cag gtg ctg tcc cag tgg gaa atc tgc ctg tcc atc gtc       528
Phe Thr Phe Gln Val Leu Ser Gln Trp Glu Ile Cys Leu Ser Ile Val
                165                 170                 175 tcc tcc tca agg ggc cag gtc cga cgc tcc ctg ggc ttc tgt gac acc       576
Ser Ser Ser Arg Gly Gln Val Arg Arg Ser Leu Gly Phe Cys Asp Thr
            180                 185                 190
```

-continued

```
acc aac aag ggg ctc ttc cag gtg gtg tca ggg ggc atg gtg ctt cag        624
Thr Asn Lys Gly Leu Phe Gln Val Val Ser Gly Gly Met Val Leu Gln
        195                 200                 205 ctg cag cag ggt gac cag gtc tgg gtt gaa aaa gac ccc aaa aag ggt        672
Leu Gln Gln Gly Asp Gln Val Trp Val Glu Lys Asp Pro Lys Lys Gly
    210                 215                 220 cac att tac cag ggc tct gag gcc gac agc gtc ttc agc ggc ttc ctc        720
His Ile Tyr Gln Gly Ser Glu Ala Asp Ser Val Phe Ser Gly Phe Leu
225                 230                 235                 240 atc ttc cca tct gcc tgagccaggg aaggacccccc tccccaccc acctctctgg        775
Ile Phe Pro Ser Ala
                245 cttccatgct ccgcctgtaa aatggggggcg ctattgcttc agctgctgaa gggagggggc    835 tggctctgag agcccccagga ctggctgccc cgtgacacat gctctaagaa gctcgtttct    895 tagacctctt cctggaataa acatctgtgt ctgtgtctgc tgaaaaaaaa aaaaaaaaaa     955
```

<210> SEQ ID NO 7
<211> LENGTH: 245
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

```
Met Glu Gly Pro Arg Gly Trp Leu Val Leu Cys Val Leu Ala Ile Ser
1               5                   10                  15

Leu Ala Ser Met Val Thr Glu Asp Leu Cys Arg Ala Pro Asp Gly Lys
            20                  25                  30

Lys Gly Glu Ala Gly Arg Pro Gly Arg Arg Gly Arg Pro Gly Leu Lys
        35                  40                  45

Gly Glu Gln Gly Glu Pro Gly Ala Pro Gly Ile Arg Thr Gly Ile Gln
    50                  55                  60

Gly Leu Lys Gly Asp Gln Gly Glu Pro Gly Pro Ser Gly Asn Pro Gly
65                  70                  75                  80

Lys Val Gly Tyr Pro Gly Pro Ser Gly Pro Leu Gly Ala Arg Gly Ile
                85                  90                  95

Pro Gly Ile Lys Gly Thr Lys Gly Ser Pro Gly Asn Ile Lys Asp Gln
            100                 105                 110

Pro Arg Pro Ala Phe Ser Ala Ile Arg Arg Asn Pro Pro Met Gly Gly
        115                 120                 125

Asn Val Val Ile Phe Asp Thr Val Ile Thr Asn Gln Glu Glu Pro Tyr
    130                 135                 140

Gln Asn His Ser Gly Arg Phe Val Cys Thr Val Pro Gly Tyr Tyr Tyr
145                 150                 155                 160

Phe Thr Phe Gln Val Leu Ser Gln Trp Glu Ile Cys Leu Ser Ile Val
                165                 170                 175

Ser Ser Ser Arg Gly Gln Val Arg Arg Ser Leu Gly Phe Cys Asp Thr
            180                 185                 190

Thr Asn Lys Gly Leu Phe Gln Val Val Ser Gly Gly Met Val Leu Gln
        195                 200                 205

Leu Gln Gln Gly Asp Gln Val Trp Val Glu Lys Asp Pro Lys Lys Gly
    210                 215                 220

His Ile Tyr Gln Gly Ser Glu Ala Asp Ser Val Phe Ser Gly Phe Leu
225                 230                 235                 240
```

```
Ile Phe Pro Ser Ala
                245
```

ASSESSING RESPONSE TO ANTI-CD20 THERAPY BY GENOTYPING C1Q COMPONENTS

This application claims benefit of priority to U.S. Provisional Appln. Ser. No. 60/709,393, filed Aug. 18, 2005, the entire contents of which are hereby incorporated by reference.

This invention was made with government support under SPORE Developmental Research Project P50 CA097274 awarded by the National Institutes of Health. The government has certain rights in the invention.

BACKGROUND OF THE INVENTION

1. Field of the Invention

The present invention relates generally to the fields of protein biology, immunology and oncology. More particularly, it concerns predicting the response of a patient to anti-CD20 antibody therapy by assessing a C1qA genotype.

2. Description of Related Art

Anti-tumor antibodies can impede tumor growth and spreading by inducing complement-mediated lysis (Gelderman et al., 2004; Harjunpaa et al., 2000; Hakulinen and Meri, 1998), mediating antibody-dependent cellular cytotoxicity (Eccles, 2001), or directly triggering cell cycle arrest and apoptosis of tumor cells (Racila et al., 1995). In vitro and animal model studies suggest that complement factors and complement inhibitors can amend the immune response to tumors, and could be important in determining the response to cancer immunotherapy (Caragine et al., 2002a; Fishelson et al., 2003; Caragine et al., 2002b; Jurianz et al., 1999; Golay et al., 2000). Complement fractions may also play an indirect role in cell-mediated cytotoxicity by recruiting the effector cells at the site of inflammation, infection or tumor development (Tazawa et al., 2003; Baldwin et al., 1999; Onoe et al., 2002).

The complement system is a key component of the immune response, and can contribute to the anti-tumor immune response (Hakulinen and Meri, 1998). A number of reports indicate that the ability of cancer to escape complement-induced lysis correlates with expression of membrane-bound complement regulatory proteins (Fishelson et al., 2003; Gorter and Meri, 1999; Donin et al., 2003). ADCC activity can be enhanced by complement receptor 3 binding to iC3b, a product of early complement activation starting with C1q in the presence of tumor specific antibody, thus enhancing FcγR-mediated effector-cell binding (Gelderman et al., 2004). However, little is known about whether heterogeneity in the host's complement system itself has an impact on anti-tumor immunity.

SUMMARY OF THE INVENTION

Thus, in accordance with the present invention, there is provided a method of assessing the response of a patient to an anti-CD20 antibody comprising (a) assessing a C1qA nucleic acid sequence from said cell, and (b) correlating the assessed C1qA nucleic acid sequence with pre-determined response potential, such as duration of response. Assessing may comprise sequencing, primer extension, differential hybridization, RFLP analysis, SNP analysis, molecular beacon analysis, and mass spectrometry, and more specifically PCR-based sequencing of a portion of the C1qA genomic sequence or cDNA. The assessing may comprise examining a C1qA exon 2, and in particular, C1qA base 276 of Gene ID NO 712, locus tag HGNC:1241 (SEQ ID NO:6).

The anti-CD20 antibody may be a monoclonal antibody, a chimeric antibody, and/or may comprise murine variable regions and human constant regions. The patient may have a lymphoma, follicular lymphoma, non-Hodgkin's lymphoma, lymphoplasmacytoid lymphomas, marginal zone lymphomas (monocytoid, splenic, mucosa-associated), diffuse large-cell lymphomas (primary mediastinal, follicular large, anaplastic large), Burkitt's lymphoma, mantle cell lymphoma, lymphoblastic lymphoma, leukemia, or chronic lymphocytic leukemia.

The method may further comprise obtaining genomic DNA from a subject. The patient may or may not have been previously diagnosed with cancer. The patient may or may not have previously been treated with an anti-CD20 antibody. The method may further comprise making a treatment decision based on step (b). The method may further comprise treating said patient, e.g., treating with anti-CD20 antibody. Treating may also comprise surgery, chemotherapy, radiotherapy, hormonal therapy, immunotherapy other than anti-CD20 antibody, cytokine therapy or gene therapy. The patient may be a human.

In another embodiment, there is provided a kit comprising (a) a pair of C1qA-derived primers that together amplify base 276 of SEQ ID NO:6; and (b) a polymerase. The kit may further comprise dNTPs, a restriction enzyme, and or one or more buffers.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions and kits of the invention can be used to achieve methods of the invention.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
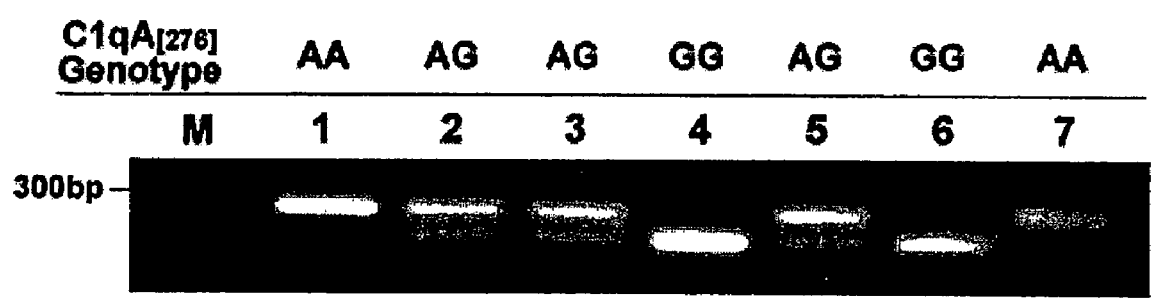
FIG. 1 RFLP Analysis of C1qA$_{[276A]}$. Enzymatic digestion of the 338 base C1qA PCR™ product was performed with ApaI. Four fragments (from 7 bp to 269 bp) are generated with the 276G allele, with the largest being visualized on agarose gels. The 276A allele lacks an ApaI site, producing a longer (288 bp) fragment.

The present inventors have previously shown that a polymorphism in the C1q component of complement appears to be associated with subcutaneous lupus erythematosus (Racila et al., 2003). Specifically, patients with lupus had a higher than expected incidence of homozygous $C1qA_{[276A]}$ SNP. The $C1qA_{[276]}$ G for A substitution is a synonymous SNP of the third base of the codon for Gly92. While it was previously thought such polymorphisms are "silent," there is now clear evidence that "synonymous" SNPs can alter the expression or function of a protein. For example, synonymous SNPs within the DRD2 transcript reduce the stability of the mRNA and, consequently, the expression of the dopamine receptor (Duan et al., 2003). Another mechanism that would lead to functional effects from a synonymous SNP is biased codon usage (Carlini et al., 2001). SNPs located within introns, that were similarly considered to have no functional effect, were shown to participate in the activation of alternative splicing mechanisms leading to generation of mRNA isoforms or exon skipping (von Ahsen and Oellerich, 2004; Webb et al., 2003; Khan et al., 2002; Modrek et al., 2001; Emmert et al., 2001). The inventors currently are exploring the possibility that the $C1qA_{[276]}$ SNP impacts on proper recognition of the intron/exon boundary. Additional studies aimed at defining prevalent haplotypes along with the end result of in vitro transcription and splicing experiments will directly address this hypothesis. The possibility that translation of alternative splicing messages of C1q leads to a reduced rate of clearance of tumor cells in the presence of therapeutic monoclonal antibody, therefore allowing other components of the immune system to become competent and participate in the anti-tumor response after completion of mAb therapy, is also addressed in ongoing studies.

More recently, the inventors showed that a genetic polymorphism in complement appears to impact on the pattern of metastatic disease in cancer. Thus, systemic metastasis from breast cancer, defined as disease that could only occur by hematogenous spread of malignant cells that had passed through the pulmonary circulation, was statistically less common in patients with the homozygous $C1qA_{[276A]}$ SNP than in patients that were heterozygous or homozygous for $C1qA_{[276G]}$. This polymorphism remained significant after adjusting for number of positive lymph nodes, estrogen-receptor status, or progesterone-receptor status. This raises the hypothesis that patients who are homozygous for $C1qA_{[276A]}$ can more effectively clear circulating malignant cells, and render the shading process of primary or metastatic tumor sites less likely to lead to systemic dissemination.

Thousands of patients with non-Hodgkin's lymphoma currently benefit from therapy with monoclonal antibodies directed against surface CD20 antigen of B-cell lymphomas. The mechanism of action of these antibodies may include complement-lysis, ADCC activation or directly induced apoptosis. Rituximab (Rituxan) is the first monoclonal antibody approved by the Food and Drug Administration for cancer immunotherapy and represents the single largely used antibody in the treatment of relapsed indolent NHL. The inventors hypothesized that lymphoma patients who are carriers of the A allele of C1qA276 polymorphism will have a better response to monoclonal antibody therapy than those who are heterozygous or homozygous $C1qA_{[276G]}$. This hypothesis was explored by evaluating whether there is an association between the $C1qA_{[276A/G]}$ genotype and clinical response to Rituximab in patients with follicular lymphoma. The rationale for this study was that determination of the C1qA genotype could be used as a valid approach to predict clinical response to antibody therapy if an association between complement polymorphisms and clinical outcome in non-Hodgkin's subjects receiving anti-CD20 therapy was established.

This work explores a direct, potential causal, relationship between clinical response to monoclonal antibody-based immunotherapy and C1qA, the initiating factor of the complement cascade in the presence of antigen-antibody complexes. It also expands on extensive data obtained in the inventors' laboratory regarding the association between genetic variations of C1qA and clinical outcome in patients with breast carcinoma (data already included in the provisional patent application). The results show that that there is an association between the A allele and better/prolonged remission after Rituximab therapy. Although the sample size is rather small, a statistically significant association of the A allele and overall response to therapy is expected if the sample size is increased.

I. C1qA

The C1qA gene encodes a major constituent of the human complement subcomponent C1q. C1q associates with C1r and C1s in order to yield the first component of the serum complement system. Deficiency of C1q has been associated with lupus erythematosus and glomerulonephritis. C1q is composed of 18 polypeptide chains: six A-chains, six B-chains, and six C-chains. Each chain contains a collagen-like region located near the N terminus and a C-terminal globular region. The A-, B-, and C-chains are arranged in the order A-C-B on chromosome 1. This gene encodes the A-chain polypeptide of human complement subcomponent C1q. The C1QA gene, also known as C1QG, C1QC or 1__22432576, maps on chromosome 1, at 1p36.11. It covers 11.51 kB on the direct strand. The C1q is found in 9 isoforms from this gene, and 25 other genes in the database also contain this motif.

The gene contains 10 confirmed introns, 9 of which are alternative. Comparison to the genome sequence shows that 9 introns follow the consensual [gt-ag] rule, 1 is atypical with good support [cc-ct]. There are 4 probable alternative promotors and 2 non-overlapping alternative last exons. The transcripts appear to differ by truncation of the 5' end, truncation of the 3' end, presence or absence of a cassette exon, because an internal intron is not always spliced out.

C1q is a subunit of the C1 enzyme complex that activates the serum complement system. C1q comprises 6 A, 6 B and 6 C chains. These share the same topology, each possessing a small, globular N-terminal domain, a collagen-like Gly/Pro-rich central region, and a conserved C-terminal region, the C1q globular domain. The C1q protein is produced in collagen-producing cells and shows sequence and structural similarity to collagens VIII and X. The collagen triple helix repeat motif is found in 9 isoforms from this gene. Eighty-two other genes in the database also contain this motif.

Members of this family belong to the collagen superfamily. Collagens are generally extracellular structural proteins involved in formation of connective tissue structure. The sequence is predominantly repeats of the G-X-Y and the polypeptide chains form a triple helix. The first position of the repeat is glycine, the second and third positions can be any residue but are frequently proline and hydroxyproline. Collagens are post-translationally modified by proline hydroxylase to form the hydroxyproline residues. Defective hydroxylation is the cause of scurvy. Some members of the collagen superfamily are not involved in connective tissue structure but share the same triple helical structure.

II. Assessing Nucleic Acids

In accordance with the present invention, one may assay C1qA nucleic acid structure. A variety of techniques, such as DNA sequencing, primer extension, RFLP analysis, differential hybridization, molecular beacon analysis and mass spectrometry may be employed.

A. Sequencing

DNA sequences may be determined by Sanger di-deoxy sequencing methods (Sanger et al., 1977). DNA polymerases are used in these methods to catalyze the extension of the nucleic acid chains. However, in its natural form, *Thermus aquaticus* DNA polymerase (like many other polymerases) includes a domain for 5'-exonuclease activity. This associated exonuclease activity can, under certain conditions including the presence of a slight excess of enzyme or if excess incubation time is employed, remove 1 to 3 nucleotides from the 5' end of the sequencing primer, causing each band in an α-labeled sequencing gel to appear more or less as a multiplier. If the label of the sequencing gel is 5', the exonuclease would not be able to cause multipliers, but it would instead reduce the signal. As a result of the deletion of the N-terminal 280 amino acid residues of *Thermus aquaticus* DNA polymerase, Klentaq-278 has no exonuclease activity and it avoids the sequencing hazards caused by 5'-exonuclease activity. Klentaq-278 can be used effectively in thermostable DNA polymerase DNA sequencing. There are basically two types of dideoxy-DNA sequencing that Klentaq-278 works well with—original dideoxy (Sanger et al., 1988) and cycle sequencing.

B. Primer Extension

In primer extension, oligonucleotides are used to assess variation in sequence at a predetermined position thereof relative to a nucleic acid, the sequence of which is known. A sample oligonucleotide is provided as a single stranded molecule, the single stranded molecule is mixed with an inducing agent, a labeled nucleotide, and a primer having a sequence identical to a region flanking the predetermined position to form a mixture, the mixture having an essential absence of nucleotides constituted of bases other than the base of which the labeled nucleotide is constituted. The mixture is then subjected to conditions conducive for the annealing of the primer to the single-stranded molecule and the formation of a primer extension product incorporating the labeled nucleotide, and the mixture is analyzed for the presence of primer extension product containing labeled nucleotide (U.S. Pat. No. 5,846,710).

C. RFLP Analysis

Restriction fragment length polymorphism, or RFLP, analysis is used to identify a change in the genetic sequence that occurs at a site where a restriction enzyme cuts. RFLPs can be used to trace inheritance patterns, identify specific mutations, and for other molecular genetic techniques. Restriction enzymes recognize specific short sequences of DNA and cut the DNA at those sites. The normal function of these enzymes in bacteria is to protect the organism by attacking foreign DNA, such as viruses.

A restriction enzyme having a predetermined sequence specificity is added to DNA being analyzed and incubated, allowing the restriction enzyme to cut at its recognition sites. The DNA is then run through a gel, which separates the DNA fragments according to size. One then visualizes the size of the DNA fragments to assess whether or not the DNA was cut by the enzyme, thereby revealing the presence or absence of a given restriction site, and hence the sequence at a given position.

D. Molecular Beacon

Molecular beacons are single-stranded oligonucleotide hybridization probes that form a stem-and-loop structure. The loop contains a probe sequence that is complementary to a target sequence, and the stem is formed by the annealing of complementary arm sequences that are located on either side of the probe sequence. A fluorophore is covalently linked to the end of one arm and a quencher is covalently linked to the end of the other arm. Molecular beacons do not fluoresce when they are free in solution. However, when they hybridize to a nucleic acid strand containing a target sequence they undergo a conformational change that enables them to fluoresce brightly.

In the absence of targets, the probe is dark, because the stem places the fluorophore so close to the nonfluorescent quencher that they transiently share electrons, eliminating the ability of the fluorophore to fluoresce. When the probe encounters a target molecule, it forms a probe-target hybrid that is longer and more stable than the stem hybrid. The rigidity and length of the probe-target hybrid precludes the simultaneous existence of the stem hybrid. Consequently, the molecular beacon undergoes a spontaneous conformational reorganization that forces the stem hybrid to dissociate and the fluorophore and the quencher to move away from each other, restoring fluorescence.

Molecular beacons can be synthesized that possess differently colored fluorophores, enabling assays to be carried out that simultaneously detect different targets in the same reaction. For example, multiplex assays can contain a number of different primer sets, each set enabling the amplification of a unique gene sequence from a different pathogenic agent, and a corresponding number of molecular beacons can be present, each containing a probe sequence specific for one of the amplicons, and each labeled with a fluorophore of a different color. The color of the resulting fluorescence, if any, identifies the pathogenic agent in the sample, and the number of amplification cycles required to generate detectable fluorescence provides a quantitative measure of the number of target organisms present. If more than one type of pathogen is present in the sample, the fluorescent colors that occur identify which are present. Moreover, due to the inherent design of gene amplification assays, the use of molecular beacons enables the abundance of a rare pathogen to be determined in the presence of a much more abundant pathogen.

In summary, molecular beacons have three key properties that enable the design of new and powerful diagnostic assays: 1) they only fluoresce when bound to their targets, 2) they can be labeled with a fluorophore of any desired color, and 3) they are so specific that they easily discriminate single-nucleotide polymorphisms. Now that a number of new and versatile spectrofluorometric thermal cyclers are available to clinical diagnostic and research laboratories, assays that simultaneously utilize as many as seven differently colored molecular beacons can be designed. This enables cost-efficient multiplex assays to be developed that identify several single nucleotide polymorphisms in one assay of a genomic DNA sample.

E. Mass Spectrometry

Mass spectrometry (MS) has emerged as a powerful tool in DNA sequencing. Mass spectrometers produce a direct mass measurement, which can be acquired in seconds or minutes in the femtomolar to picomolar range. Matrix-assisted laser desorption/ionization (MALDI) time-of-flight (TOF) MS has been successfully used for fast DNA sequencing and the efficient size determination of DNA molecules. The advent of MALDI-TOF MS has made it easier to ionize intact large DNA molecules and measure their mass-to-charge ratios. Single-stranded and double-stranded polymerase chain reaction (PCR™) products of 500 nucleotide (nt) in length have been detected by MALDI-TOF MS. Using optimized matrix-laser combinations that reduce DNA fragmentation, infrared MALDI mass spectra of synthetic DNA, restriction enzyme fragments of plasmid DNA, and RNA transcripts up to a size of 2180 nt have been reported with an accuracy of +/−0.5-1%. Although large oligomers have been detected by MALDI-TOF MS, it is generally accepted that up to a 100-mer is routine at present. Except for DNA sequencing, there is at present no technique capable of directly relating the molecular weight of a DNA molecule to its base composition. See U.S. Pat. No. 6,585,739.

F. Hybridization

Hybridization is defined as the ability of a nucleic acid to selectively form duplex molecules with complementary stretches of DNAs and/or RNAs. Depending on the application envisioned, one would employ varying conditions of hybridization to achieve varying degrees of selectivity of the probe or primers for the target sequence.

Typically, a probe or primer of between 13 and 100 nucleotides, preferably between 17 and 100 nucleotides in length up to 1-2 kilobases or more in length will allow the formation of a duplex molecule that is both stable and selective. Molecules having complementary sequences over contiguous stretches greater than 20 bases in length are generally preferred, to increase stability and selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, lower stringency conditions may be used. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, calorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™ or Northern blotting, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

G. Amplification of Nucleic Acids

Since many mRNAs are present in relatively low abundance, nucleic acid amplification greatly enhances the ability to assess expression. The general concept is that nucleic acids can be amplified using paired primers flanking the region of interest. The term "primer," as used herein, is meant to encompass any nucleic acid that is capable of priming the synthesis of a nascent nucleic acid in a template-dependent process. Typically, primers are oligonucleotides from ten to twenty or thirty base pairs in length, but longer sequences can be employed. Primers may be provided in double-stranded and/or single-stranded form, although the single-stranded form is preferred.

Pairs of primers designed to selectively hybridize to nucleic acids corresponding to selected genes are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals.

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

A reverse transcriptase PCR™ amplification procedure may be performed to quantify the amount of mRNA amplified. Methods of reverse transcribing RNA into cDNA are well known (see Sambrook et al., 1989). Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Whereas standard PCR™ usually uses one pair of primers to amplify a specific sequence, multiplex-PCR (MPCR) uses multiple pairs of primers to amplify many sequences simultaneously (Chamberlan et al., 1990). The presence of many PCR™ primers in a single tube could cause many problems, such as the increased formation of misprimed PCR™ products and "primer dimers," the amplification discrimination of longer DNA fragment and so on. Normally, MPCR buffers contain a Taq Polymerase additive, which decreases the competition among amplicons and the amplification discrimination of longer DNA fragment during MPCR. MPCR products can further be hybridized with gene-specific probe for verification. Theoretically, one should be able to use as many as primers as necessary. However, due to side effects (primer dimers, misprimed PCR™ products, etc.) caused during MPCR, there is a limit (less than 20) to the number of primers that can be used in a MPCR reaction. See also European Application No. 0 364 255 and Mueller & Wold (1989).

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). European Application No. 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race," "real time" and "one-sided PCR™" (Frohman, 1990; Ohara et al., 1989).

H. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 1989). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

I. Nucleic Acid Arrays

Microarrays comprise a plurality of polymeric molecules spatially distributed over, and stably associated with, the surface of a substantially planar substrate, e.g., biochips. Microarrays of polynucleotides have been developed and find use in a variety of applications, such as screening and DNA sequencing. One area in particular in which microarrays find use is in gene expression analysis.

In gene expression analysis with microarrays, an array of "probe" oligonucleotides is contacted with a nucleic acid sample of interest, i.e., target, such as polyA mRNA from a particular tissue type. Contact is carried out under hybridization conditions and unbound nucleic acid is then removed. The resultant pattern of hybridized nucleic acid provides information regarding the genetic profile of the sample tested. Methodologies of gene expression analysis on microarrays are capable of providing both qualitative and quantitative information.

A variety of different arrays that may be used are known in the art. The probe molecules of the arrays which are capable of sequence specific hybridization with target nucleic acid may be polynucleotides or hybridizing analogues or mimetics thereof, including: nucleic acids in which the phosphodiester linkage has been replaced with a substitute linkage, such as phophorothioate, methylimino, methylphosphonate, phosphoramidate, guanidine and the like; nucleic acids in which the ribose subunit has been substituted, e.g., hexose phosphodiester; peptide nucleic acids; and the like. The length of the probes will generally range from 10 to 1000 nts, where in some embodiments the probes will be oligonucleotides and usually range from 15 to 150 nts and more usually from 15 to 100 nts in length, and in other embodiments the probes will be longer, usually ranging in length from 150 to 1000 nts, where the polynucleotide probes may be single- or double-stranded, usually single-stranded, and may be PCR™ fragments amplified from cDNA.

The probe molecules on the surface of the substrates will correspond to selected genes being analyzed and be positioned on the array at a known location so that positive hybridization events may be correlated to expression of a particular gene in the physiological source from which the target nucleic acid sample is derived. The substrates with which the probe molecules are stably associated may be fabricated from a variety of materials, including plastics, ceramics, metals, gels, membranes, glasses, and the like. The arrays may be produced according to any convenient methodology, such as preforming the probes and then stably associating them with the surface of the support or growing the probes directly on the support. A number of different array configurations and methods for their production are known to those of skill in the art and disclosed in U.S. Pat. Nos. 5,445,934, 5,532,128, 5,556,752, 5,242,974, 5,384,261, 5,405,783, 5,412,087, 5,424,186, 5,429,807, 5,436,327, 5,472,672, 5,527,681, 5,529,756, 5,545,531, 5,554,501, 5,561,071, 5,571,639, 5,593,839, 5,599,695, 5,624,711, 5,658,734, 5,700,637, and 6,004,755.

Following hybridization, where non-hybridized labeled nucleic acid is capable of emitting a signal during the detection step, a washing step is employed where unhybridized labeled nucleic acid is removed from the support surface, generating a pattern of hybridized nucleic acid on the substrate surface. A variety of wash solutions and protocols for their use are known to those of skill in the art and may be used.

Where the label on the target nucleic acid is not directly detectable, one then contacts the array, now comprising bound target, with the other member(s) of the signal producing system that is being employed. For example, where the label on the target is biotin, one then contacts the array with streptavidin-fluorescer conjugate under conditions sufficient for binding between the specific binding member pairs to occur. Following contact, any unbound members of the signal producing system will then be removed, e.g., by washing. The specific wash conditions employed will necessarily depend on the specific nature of the signal producing system that is employed, and will be known to those of skill in the art familiar with the particular signal producing system employed.

The resultant hybridization pattern(s) of labeled nucleic acids may be visualized or detected in a variety of ways, with the particular manner of detection being chosen based on the particular label of the nucleic acid, where representative detection means include scintillation counting, autoradiography, fluorescence measurement, calorimetric measurement, light emission measurement and the like.

Prior to detection or visualization, where one desires to reduce the potential for a mismatch hybridization event to generate a false positive signal on the pattern, the array of hybridized target/probe complexes may be treated with an endonuclease under conditions sufficient such that the endonuclease degrades single stranded, but not double stranded DNA. A variety of different endonucleases are known and may be used, where such nucleases include: mung bean nuclease, SI nuclease, and the like. Where such treatment is employed in an assay in which the target nucleic acids are not labeled with a directly detectable label, e.g., in an assay with biotinylated target nucleic acids, the endonuclease treatment will generally be performed prior to contact of the array with the other member(s) of the signal producing system, e.g., fluorescent-streptavidin conjugate. Endonuclease treatment, as described above, ensures that only end-labeled target/probe complexes having a substantially complete hybridization at the 3' end of the probe are detected in the hybridization pattern.

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding the signal emitted by known number of end-labeled target nucleic acids to obtain a count or absolute value of the copy number of each end-labeled target that is hybridized to a particular spot on the array in the hybridization pattern.

III. Assessing Protein Structure

In accordance with the present invention, assessment of C1qA can be made at the protein level, rather than the nucleic acid level. A variety of techniques may be employed to interrogate protein structure, as discussed below.

A. Immunodetection

There are a variety of methods that can be used to assess protein structure. One such approach is to perform protein/epitope identification with the use of antibodies. As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting. The term "antibody" also refers to any antibody-like molecule that has an antigen binding region, and includes antibody fragments such as Fab', Fab, $F(ab')_2$, single domain antibodies (DABs), Fv, scFv (single chain Fv), and the like. The techniques for preparing and using various antibody-based constructs and fragments are well known in the art. Means for preparing and characterizing antibodies, both polyclonal and monoclonal, are also well known in the art (see, e.g., Antibodies: A Laboratory Manual, 1988; incorporated herein by reference). In particular, antibodies to calcyclin, calpactin I light chain, astrocytic phosphoprotein PEA-15 and tubulin-specific chaperone A are contemplated.

In accordance with the present invention, immunodetection methods are provided. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. The steps of various useful immunodetection methods have been described in the scientific literature, such as, e.g., Doolittle and Ben-Zeev, 1999; Gulbis and Galand, 1993; De Jager et al., 1993; and Nakamura et al., 1987, each incorporated herein by reference.

In general, the immunobinding methods include obtaining a sample suspected of containing a relevant polypeptide, and contacting the sample with a first antibody under conditions effective to allow the formation of immunocomplexes. In terms of antigen detection, the biological sample analyzed may be any sample that is suspected of containing an antigen, such as, for example, a tissue section or specimen, a homogenized tissue extract, a cell, or even a biological fluid.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to, any antigens present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the antibody is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection designed by Charles Cantor uses two different antibodies. A first step biotinylated, monoclonal or polyclonal antibody is used to detect the target antigen(s), and a second step antibody is then used to detect the biotin attached to the complexed biotin. In that method the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR™ method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR™ reaction with suitable primers with appropriate controls. At least in theory, the enormous amplification capability and specificity of PCR™ can be utilized to detect a single antigen molecule.

As detailed above, immunoassays are in essence binding assays. Certain immunoassays are the various types of enzyme linked immunosorbent assays (ELISAs) and radioimmunoassays (RIA) known in the art. However, it will be readily appreciated that detection is not limited to such techniques, and Western blotting, dot blotting, FACS analyses, and the like may also be used.

In one exemplary ELISA, the antibodies of the invention are immobilized onto a selected surface exhibiting protein affinity, such as a well in a polystyrene microtiter plate. Then, a test composition suspected of containing the antigen, such as a clinical sample, is added to the wells. After binding and washing to remove non-specifically bound immune complexes, the bound antigen may be detected. Detection is generally achieved by the addition of another antibody that is linked to a detectable label. This type of ELISA is a simple "sandwich ELISA". Detection may also be achieved by the addition of a second antibody, followed by the addition of a third antibody that has binding affinity for the second antibody, with the third antibody being linked to a detectable label.

In another exemplary ELISA, the samples suspected of containing the antigen are immobilized onto the well surface and then contacted with the anti-ORF message and anti-ORF translated product antibodies of the invention. After binding and washing to remove non-specifically bound immune complexes, the bound anti-ORF message and anti-ORF translated product antibodies are detected. Where the initial anti-ORF message and anti-ORF translated product antibodies are linked to a detectable label, the immune complexes may be detected directly. Again, the immune complexes may be detected using a second antibody that has affinity for the first anti-ORF message and anti-ORF translated product antibody, with the second antibody being linked to a detectable label.

Another ELISA in which the antigens are immobilized, involves the use of antibody competition in the detection. In this ELISA, labeled antibodies against an antigen are added to the wells, allowed to bind, and detected by means of their label. The amount of an antigen in an unknown sample is then determined by mixing the sample with the labeled antibodies against the antigen during incubation with coated wells. The presence of an antigen in the sample acts to reduce the amount of antibody against the antigen available for binding to the well and thus reduces the ultimate signal. This is also appropriate for detecting antibodies against an antigen in an unknown sample, where the unlabeled antibodies bind to the antigen-coated wells and also reduces the amount of antigen available to bind the labeled antibodies.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background. The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

The antibodies of the present invention may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and/or is well known to those of skill in the art (Brown et al., 1990; Abbondanzo et al., 1999; Allred et al., 1990).

Also contemplated in the present invention is the use of immunohistochemistry. This approach uses antibodies to detect and quantify antigens in intact tissue samples. Generally, frozen-sections are prepared by rehydrating frozen "pulverized" tissue at room temperature in phosphate buffered saline (PBS) in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25-50 serial sections.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and cutting up to 50 serial permanent sections.

B. Protein-Based Detection—Mass Spectromety

By exploiting the intrinsic properties of mass and charge, mass spectrometry (MS) can resolved and confidently identified a wide variety of complex compounds, including proteins. Traditional quantitative MS has used electrospray ionization (ESI) followed by tandem MS (MS/MS) (Chen et al., 2001; Zhong et al., 2001; Wu et al., 2000) while newer quantitative methods are being developed using matrix assisted laser desorption/ionization (MALDI) followed by time of flight (TOF) MS (Bucknall et al., 2002; Mirgorodskaya et al., 2000; Gobom et al., 2000). In accordance with the present invention, one can generate mass spectrometry profiles that are useful for determining the structure of C1qa proteins.

1. ESI

ESI is a convenient ionization technique developed by Fenn and colleagues (Fenn et al., 1989) that is used to produce gaseous ions from highly polar, mostly nonvolatile biomolecules, including lipids. The sample is injected as a liquid at low flow rates (1-10 μL/min) through a capillary tube to which a strong electric field is applied. The field generates additional charges to the liquid at the end of the capillary and produces a fine spray of highly charged droplets that are electrostatically attracted to the mass spectrometer inlet. The evaporation of the solvent from the surface of a droplet as it travels through the desolvation chamber increases its charge density substantially. When this increase exceeds the Rayleigh stability limit, ions are ejected and ready for MS analysis.

A typical conventional ESI source consists of a metal capillary of typically 0.1-0.3 mm in diameter, with a tip held approximately 0.5 to 5 cm (but more usually 1 to 3 cm) away from an electrically grounded circular interface having at its center the sampling orifice, such as described by Kabarle et al. (1993). A potential difference of between 1 to 5 kV (but more typically 2 to 3 kV) is applied to the capillary by power supply to generate a high electrostatic field ($10^6$ to $10^7$ V/m) at the capillary tip. A sample liquid carrying the analyte to be analyzed by the mass spectrometer, is delivered to tip through an internal passage from a suitable source (such as from a chromatograph or directly from a sample solution via a liquid flow controller). By applying pressure to the sample in the capillary, the liquid leaves the capillary tip as a small highly electrically charged droplets and further undergoes desolvation and breakdown to form single or multicharged gas phase ions in the form of an ion beam. The ions are then collected by the grounded (or negatively charged) interface plate and led through an the orifice into an analyzer of the mass spectrometer. During this operation, the voltage applied to the capillary is held constant. Aspects of construction of ESI sources are described, for example, in U.S. Pat. Nos. 5,838,002; 5,788,166; 5,757,994; RE 35,413; and 5,986,258.

2. ESI/MS/MS

In ESI tandem mass spectroscopy (ESI/MS/MS), one is able to simultaneously analyze both precursor ions and product ions, thereby monitoring a single precursor product reaction and producing (through selective reaction monitoring (SRM)) a signal only when the desired precursor ion is present. When the internal standard is a stable isotope-labeled version of the analyte, this is known as quantification by the stable isotope dilution method. This approach has been used to accurately measure pharmaceuticals (Zweigenbaum et al., 2000; Zweigenbaum et al., 1999) and bioactive peptides (Desiderio et al., 1996; Lovelace et al., 1991). Newer methods are performed on widely available MALDI-TOF instruments, which can resolve a wider mass range and have been used to quantify metabolites, peptides, and proteins. Larger molecules such as peptides can be quantified using unlabeled homologous peptides as long as their chemistry is similar to the analyte peptide (Duncan et al., 1993; Bucknall et al., 2002). Protein quantification has been achieved by quantifying tryptic peptides (Mirgorodskaya et al., 2000). Complex mixtures such as crude extracts can be analyzed, but in some instances sample clean up is required (Nelson et al., 1994; Gobom et al., 2000).

3. SIMS

Secondary ion mass spectroscopy, or SIMS, is an analytical method that uses ionized particles emitted from a surface for mass spectroscopy at a sensitivity of detection of a few parts per billion. The sample surface is bombarded by primary energetic particles, such as electrons, ions (e.g., O, Cs), neutrals or even photons, forcing atomic and molecular particles to be ejected from the surface, a process called sputtering. Since some of these sputtered particles carry a charge, a mass spectrometer can be used to measure their mass and charge. Continued sputtering permits measuring of the exposed elements as material is removed. This in turn permits one to construct elemental depth profiles. Although the majority of secondary ionized particles are electrons, it is the secondary ions which are detected and analysis by the mass spectrometer in this method.

4. LD-MS and LDLPMS

Laser desorption mass spectroscopy (LD-MS) involves the use of a pulsed laser, which induces desorption of sample material from a sample site—effectively, this means vaporization of sample off of the sample substrate. This method is usually only used in conjunction with a mass spectrometer, and can be performed simultaneously with ionization if one uses the right laser radiation wavelength.

When coupled with Time-of-Flight (TOF) measurement, LD-MS is referred to as LDLPMS (Laser Desorption Laser Photoionization Mass Spectroscopy). The LDLPMS method of analysis gives instantaneous volatilization of the sample, and this form of sample fragmentation permits rapid analysis without any wet extraction chemistry. The LDLPMS instrumentation provides a profile of the species present while the retention time is low and the sample size is small. In LDLPMS, an impactor strip is loaded into a vacuum chamber. The pulsed laser is fired upon a certain. spot of the sample site, and species present are desorbed and ionized by the laser radiation. This ionization also causes the molecules to break up into smaller fragment-ions. The positive or negative ions made are then accelerated into the flight tube, being detected at the end by a microchannel plate detector. Signal intensity, or peak height, is measured as a function of travel time. The applied voltage and charge of the particular ion determines the kinetic energy, and separation of fragments are due to different size causing different velocity. Each ion mass will thus have a different flight-time to the detector.

One can either form positive ions or negative ions for analysis. Positive ions are made from regular direct photoionization, but negative ion formation require a higher powered laser and a secondary process to gain electrons. Most of the molecules that come off the sample site are neutrals, and thus can attract electrons based on their electron affinity. The negative ion formation process is less efficient than forming just positive ions. The sample constituents will also affect the outlook of a negative ion spectra.

Other advantages with the LDLPMS method include the possibility of constructing the system to give a quiet baseline of the spectra because one can prevent coevolved neutrals from entering the flight tube by operating the instrument in a linear mode. Also, in environmental analysis, the salts in the air and as deposits will not interfere with the laser desorption and ionization. This instrumentation also is very sensitive, known to detect trace levels in natural samples without any prior extraction preparations.

5. MALDI-TOF-MS

Since its inception and commercial availability, the versatility of MALDI-TOF-MS has been demonstrated convincingly by its extensive use for qualitative analysis. For example, MALDI-TOF-MS has been employed for the characterization of synthetic polymers (Marie et al., 2000; Wu et al., 1998). peptide and protein analysis (Roepstorff et al., 2000; Nguyen et al., 1995), DNA and oligonucleotide sequencing (Miketova et al., 1997; Faulstich et al., 1997; Bentzley et al., 1996), and the characterization of recombinant proteins (Kanazawa et al., 1999; Villanueva et al., 1999). Recently, applications of MALDI-TOF-MS have been extended to include the direct analysis of biological tissues and single cell organisms with the aim of characterizing endogenous peptide and protein constituents (Li et al., 2000; Lynn et al., 1999; Stoeckli et al., 2001; Caprioli et al., 1997; Chaurand et al., 1999; Jespersen et al., 1999).

The properties that make MALDI-TOF-MS a popular qualitative tool—its ability to analyze molecules across an extensive mass range, high sensitivity, minimal sample preparation and rapid analysis times—also make it a potentially useful quantitative tool. MALDI-TOF-MS also enables non-volatile and thermally labile molecules to be analyzed with relative ease. It is therefore prudent to explore the potential of MALDI-TOF-MS for quantitative analysis in clinical settings, for toxicological. screenings, as well as for environmental analysis. In addition, the application of MALDI-TOF-MS to the quantification of peptides and proteins is particularly relevant. The ability to quantify intact proteins in biological tissue and fluids presents a particular challenge in the expanding area of proteomics and investigators urgently require methods to accurately measure the absolute quantity of proteins. While there have been reports of quantitative MALDI-TOF-MS applications, there are many problems inherent to the MALDI ionization process that have restricted its widespread use (Kazmaier et al., 1998; Horak et al., 2001; Gobom et al., 2000; Wang et al., 2000; Desiderio et al., 2000). These limitations primarily stem from factors such as the sample/matrix heterogeneity, which are believed to contribute to the large variability in observed signal intensities for analytes, the limited dynamic range due to detector saturation, and difficulties associated with coupling MALDI-TOF-MS to on-line separation techniques such as liquid chromatography. Combined, these factors are thought to compromise the accuracy, precision, and utility with which quantitative determinations can be made.

Because of these difficulties, practical examples of quantitative applications of MALDI-TOF-MS have been limited. Most of the studies to date have focused on the quantification of low mass analytes, in particular, alkaloids or active ingredients in agricultural or food products (Wang et al., 1999; Jiang et al., 2000; Wang et al., 2000; Yang et al., 2000; Wittmann et al., 2001), whereas other studies have demonstrated the potential of MALDI-TOF-MS for the quantification of biologically relevant analytes such as neuropeptides, proteins, antibiotics, or various metabolites in biological tissue or fluid (Muddiman et al., 1996; Nelson et al., 1994; Duncan et al., 1993; Gobom et al., 2000; Wu et al., 1997; Mirgorodskaya et al., 2000). In earlier work it was shown that linear calibration curves could be generated by MALDI-TOF-MS provided that an appropriate internal standard was employed (Duncan et al., 1993). This standard can "correct" for both sample-to-sample and shot-to-shot variability. Stable isotope labeled internal standards (isotopomers) give the best result.

With the marked improvement in resolution available on modem commercial instruments, primarily because of delayed extraction (Bahr et al., 1997; Takach et al., 1997), the opportunity to extend quantitative work to other examples is now possible; not only of low mass analytes, but also biopolymers. Of particular interest is the prospect of absolute multi-component quantification in biological samples (e.g., proteomics applications).

The properties of the matrix material used in the MALDI method are critical. Only a select group of compounds is useful for the selective desorption of proteins and polypeptides. A review of all the matrix materials available for peptides and proteins shows that there are certain characteristics the compounds must share to be analytically useful. Despite its importance, very little is known about what makes a matrix material "successful" for MALDI. The few materials that do work well are used heavily by all MALDI practitioners and new molecules are constantly being evaluated as potential matrix candidates. With a few exceptions, most of the matrix materials used are solid organic acids. Liquid matrices have also been investigated, but are not used routinely.

IV. Lymphomas

The lymphatic system is a network of organs, ducts, and nodes that interacts with the circulatory system to transport lymph throughout the body. This system contains lymphocytes—cells involved in defending the body against infectious organisms. Lymphomas are malignancies of the lymph system. They can be generally divided into two groups, Hodgkin and non-Hodgkin's lymphoma. Hodgkin's lymphoma only represents about 15% of lymphomas, with non-Hodgkin's lymphoma accounting for the remainder. Non-Hodgkin's lymphomas occur most often in lymph nodes in the chest, neck, abdomen, tonsils, and the skin, but may also develop in sites other than lymph nodes. In Americans, this most common alternate location is in the digestive tract, although primary lymphomas of the central nervous system are increasing. In Europeans, lymphomas outside the lymph nodes are more likely to develop around the tonsils.

The majority of of non-Hodgkin's lymphomas are in B-cells. Activation of Bcl-2 is believed to be partly responsible for many B-cell lymphomas—this defect prevents apoptosis in the lymphoma cells. There are more than 20 distinct types of non-Hodgkin's lymphomas. Most first arise in the lymph nodes, but about 20% to 30% of cases are now found outside the nodes, most often in the stomach, small intestine, skin, and brain.

Lymphomas are categorized in a number of ways One is know as the REAL (Revised European-American Lymphoma Classification) System. It classifies all lymphomas by appearance, cell type, and genetic make-up. Non-Hodgkin's lymphomas are first grouped into B-cell or T-cell categories. They are then further categorized by whether the B- and T-cell lymphomas malignancies were derived from immature (precursor) cells or mature (peripheral) cells. The peripheral B- and T-cells are then further classified by their appearance, genetic make-up, and specific chemical "markers" that further identify them.

Each non-Hodgkin's lymphoma is further defined by its grade, or how aggressive it is: indolent (slow-growing), also referred to as low-grade; aggressive (fast-growing), also referred to as intermediate- or high-grade. According to a 2002 report, half of new cases are now intermediate-grade lymphomas. Low-grade makes up 30% and high-grade 10% of all lymphomas. Lymphomas are also grouped by certain properties: size (large versus small); shape (round versus irregular); whether they are or resemble blood plasma cells; whether they are follicular (organized in round clusters) or diffuse (spread evenly throughout the lymph node).

Staging the disease is another important step in classifying lymphomas. The stage (I through IV) of an NHL is determined by the number of tumors and whether they are still localized or have spread beyond the lymph node. In general, the higher the stage, the poorer the outcome, but, again, other factors are important for a precise prognosis.

Slow growing lymphomas include follicular lymphomas, which account for 70% of indolent tumors and 20% of all NHLs in industrialized countries. Another slow growing lymphoma is lymphoplasmacytoid/Waldenstrom's macroglobulinemia. Often found in bone marrow, lymph nodes, and spleen, it can cause blood to become viscous and "sticky." Marginal zone lymphomas are also considered slow growing and often occur as a result of a pre-existing disorder, such as hepatitis C, infection in the stomach (*H. pylori*), or an autoimmune disorder (e.g., Sjögren's disease in the salivary glands or Hashimoto's thyroiditis in the thyroid gland). They may be classified as: monocytoid B-cell lymphoma (involves only lymph nodes); splenic marginal zone lymphoma (affects the spleen, which becomes greatly enlarged, and also blood and bone marrow); and nucosa-associated lymphoid tissue (MALT) lymphoma (involves other sites, usually the gastrointestinal tract, thyroid, lung, breast, or skin).

Aggressive lymphomas include diffuse large-cell lymphomas, which are the most common NHLs, accounting for about 40% of all cases. Subtypes include: primary mediastinal large B-cell lymphoma; follicular large cell lymphoma; anaplastic large cell lymphoma. In about 40% of cases, these lymphomas appear in areas outside lymph nodes, including digestive tract, skin, bone, thyroid, and testes.

Another aggressive lymphoma is Burkitt's lymphoma/diffuse, small noncleaved cell lymphoma. This is the most common childhood NHL. In African children, it often involves facial bones and is associated with Epstein-Barr infection. Also considered to be aggressive are mantle cell lymphoma (found in lymph nodes, the spleen, bone marrow, blood, and sometimes the gastrointestinal system (lymphomatous polyposis)), and lymphoblastic lymphoma (often occurs in young people; associated with large mediastinal mass; carries a high risk for spreading to bone marrow and central nervous system).

V. Kits

Another embodiment of the present invention is a diagnostic kit. In a non-limiting example, one or more C1qA-derived primers or probes may be comprised in a kit. The kits will thus such primers or probes in suitable container means, optionally along with additional agents of the present invention.

The kits may comprise a suitably aliquoted pair of primer that amplifies a region of interest in the C1qA gene or transcript. The primers may be labeled or unlabeled (one or both). These components may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will contain a second, third or other additional container into which the additional components may be separately placed. However, various combinations of components, such as a primer pair, may be comprised in a vial. The kits of the present invention also will typically include a means for holding the container means, such as injection or blow-molded plastic forms in which the desired container means are retained.

VI. Therapy

In another embodiment, the present invention provides for the administration of a cancer therapy based on the prediction of metastasis described above. Cancer therapies are well known to those of skill in the art and may be administered according to standard protocols depending on the experienced judgment of the clinician involved.

A. CD-20 Antibody Therapy

Anti-CD20 antibodies may be used as a primary therapy for a variety of lymphomas. The only antibody currently approved for clinical use is Rituximab, a chimeric murine/human monoclonal antibody that binds the CD20 antigen found on normal and malignant B lymphocytes. It is an $IgG_1$ kappa class immunoglobulin having murine light- and heavy-chain variable region sequences and human constant region sequences. The binding affinity for the CD20 antigen is about 8.0 nM. Rituximab is manufactured and available from Genentech, Inc., as RITUXAN®. A fully humanized version of Rituximab is currently under development.

The product is formulated for IV administration in 9.0 mg/mL sodium chloride, 7.35 mg/mL sodium citrate dihydrate, 0.7 mg/mL polysorbate 80, and Sterile Water for Injection. The pH is adjusted to 6.5.

CD20 (human B lymphocyte restricted differentiation antigen, Bp35), the target for Rituximab, is a hydrophobic transmembrane protein with a molecular weight of approximately 35 kD located on pre-B and mature B lymphocytes (Valentine er al., 1989; Einfeld et al., 1988). It also is expressed on >90% of B cell non-Hodgkin's lymphomas (NHL) (Anderson et al., 1984), but is not found on hematopoietic stem cells, pro-B cells, normal plasma cells or other normal tissues (Tedder et al., 1985). CD20 regulates an early step(s) in the activation process for cell cycle initiation and differentiation (Tedder et al., 1985), and possibly functions as a calcium ion channel (Tedder et al., 1990). CD20 is not shed from the cell surface and does not internalize upon antibody binding (Press et al., 1987). Free CD20 antigen is not found in the circulation (Einfeld et al., 1988). Rituximab binds to the CD20 antigen on B lymphocytes, and recruits immune effector functions to mediate B-cell lysis in vitro. Possible mechanisms of cell lysis include complement-dependent cytotoxicity (CDC) (Reff et al., 1994) and antibody-dependent cell mediated cytotoxicity (ADCC). The antibody has been shown to induce apoptosis in the DHL-4 human B-cell lymphoma line (Demidem et al., 1997).

RITUXAN® (Rituximab) is indicated for the treatment of patients with relapsed or refractory, low-grade or follicular, CD20-positive, B-cell non-Hodgkin's lymphoma, and contraindicated in patients with known anaphylaxis or IgE-mediated hypersensitivity to murine proteins. RITUXAN® is given at 375 $mg/m^2$ IV infusion once weekly for 4 or 8 doses in an initial treatment. For patients who subsequently develop progressive disease, they may be safely retreated with RITUXAN® 375 $mg/m^2$ IV infusion once weekly for 4 doses. Currently there are limited data concerning more than 2 courses. RITUXAN can also be used in the Zevalin therapeutic regimen. RITUXAN® 250 $mg/m^2$ should be infused within 4 hours prior to the administration of Indium-111-(In-111-) Zevalin and within 4 hours prior to the administration of Yttrium-90-(Y-90-) Zevalin. Administration of RITUXAN and In-111-Zevalin should precede RITUXAN and Y-90-Zevalin by 7-9 days.

B. Chemotherapeutic Agents

1. Antibiotics

Doxorubicin. Doxorubicin hydrochloride, 5,12-Naphthacenedione, (8s-cis )-10-((3-amino-2,3,6-trideoxy-a-L-lyxo-hexopyranosyl)oxy)-7,8,9,10-tetrahydro-6,8,11-trihydroxy-8-(hydroxyacetyl)-1-methoxy-hydrochloride (hydroxydaunorubicin hydrochloride, Adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 $mg/m^2$ at 21-day intervals or 25 to 30 $mg/m^2$ on each of 2 or 3 successive days repeated at 3- or 4-wk intervals or 20 $mg/m^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 $mg/m^2$ in patients with normal heart function and 400 $mg/m^2$ in persons having received mediastinal irradiation. Alternatively, 30 $mg/m^2$ on each of 3 consecutive days, repeated every 4 wk. Exemplary doses may be 10 $mg/m^2$, 20 $mg/m^2$, 30 $mg/m^2$, 50 $mg/m^2$, 100 $mg/m^2$, 150 $mg/m^2$, 175 $mg/m^2$, 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Daunorubicin. Daunorubicin hydrochloride, 5,12-Naphthacenedione, (8S-cis)-8-acetyl-10-((3-amino-2,3,6-trideoxy-a-L-lyxo-hexanopyranosyl)oxy)-7,8,9,10-tetrahydro-6,8,11-trihydroxy-10-methoxy-, hydrochloride; also termed cerubidine and available from Wyeth. Daunorubicin intercalates into DNA, blocks DNA-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 min and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m²/day (30 mg/m² for patients older than 60 yr) for 1, 2 or 3 days every 3 or 4 wk or 0.8 mg/kg/day for 3 to 6 days every 3 or 4 wk; no more than 550 mg/m² should be given in a lifetime, except only 450 mg/m² if there has been chest irradiation; children, 25 mg/m² once a week unless the age is less than 2 yr or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m², 20 mg/m², 30 mg/m², 50 mg/m², 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Mitomycin. Mitomycin (also known as mutamycin or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg bolus injection is 17 minutes. After injection of 30 mg, 20 mg, or 10 mg I.V., the maximal serum concentrations were 2.4 mg/mL, 1.7 mg/mL, and 0.52 mg/mL, respectively. Clearance is effected primarily by metabolism in the liver, but metabolism occurs in other tissues as well. The rate of clearance is inversely proportional to the maximal serum concentration because, it is thought, of saturation of the degradative pathways.

Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

Actinomycin D. Actinomycin D (Dactinomycin) (50-76-0); $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors which fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

Bleomycin. Bleomycin is a mixture of cytotoxic glycopeptide antibiotics isolated from a strain of *Streptomyces verticillus*. It is freely soluble in water.

Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 mL per minute, the serum or plasma terminal elimination half-life of bleomycin is approximately 115 min. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

Bleomycin may be given by the intramuscular, intravenous, or subcutaneous routes.

2. Miscellaneous Agents

Cisplatin. Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15-20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg/m$^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

In certain aspects of the current invention cisplatin is used in combination with emodin or emodin-like compounds in the treatment of non-small cell lung carcinoma. It is clear, however, that the combination of cisplatin and emodin and or emodin-like compounds could be used for the treatment of any other neu-mediated cancer.

VP16. VP16 is also know as etoposide and is used primarily for treatment of testicular tumors, in combination with bleomycin and cisplatin, and in combination with cisplatin for small-cell carcinoma of the lung. It is also active against non-Hodgkin's lymphomas, acute nonlymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m$^2$ or as little as 2 mg/m$^2$, routinely 35 mg/m$^2$, daily for 4 days, to 50 mg/m$^2$, daily for 5 days have also been used. When given orally, the dose should be doubled. Hence the doses for small cell lung carcinoma may be as high as 200-250 mg/m$^2$. The intravenous dose for testicular cancer (in combination therapy) is 50 to 100 mg/m$^2$ daily for 5 days, or 100 mg/m$^2$ on alternate days, for three doses. Cycles of therapy are usually repeated every 3 to 4 weeks. The drug should be administered slowly during a 30- to 60-min infusion in order to avoid hypotension and bronchospasm, which are probably due to the solvents used in the formulation.

Tumor Necrosis Factor. Tumor Necrosis Factor (TNF; Cachectin) is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

3. Plant Alkaloids

Taxol. Taxol is an experimental antimitotic agent, isolated from the bark of the ash tree, *Taxus brevifolia*. It binds to tubulin (at a site distinct from that used by the vinca alkaloids) and promotes the assembly of microtubules. Taxol is currently being evaluated clinically; it has activity against malignant melanoma and carcinoma of the ovary. Maximal doses are 30 mg/m$^2$ per day for 5 days or 210 to 250 mg/m$^2$ given once every 3 wk. Of course, all of these dosages are exemplary, and any dosage in-between these points is also expected to be of use in the invention.

Vincristine. Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hr. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisolone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisolone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisolone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m$^2$, 0.06 mg/m$^2$, 0.07 mg/m$^2$, 0.08 mg/m$^2$, 0.1 mg/m$^2$, 0.12 mg/m$^2$, 0.14 mg/m$^2$, 0.15 mg/m$^2$, 0.2 mg/m$^2$, 0.25 mg/m$^2$ can be given as a constant intravenous infusion. Of course, all of these dosages are exemplary, and any dosage in-between these points is also expected to be of use in the invention.

Vinblastine. When cells are incubated with vinblastine, dissolution of the microtubules occurs. Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours.

Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine for use will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

4. Alkylating Agents

Carmustine. Carmustine (sterile carmustine) is one of the nitrosoureas used in the treatment of certain neoplastic diseases. It is 1,3-bis-(2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medulloblastoma, astrocytoma, ependymoma, and metastatic brain tumors. Also it has been used in combination with prednisolone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m$^2$ intravenously every 6 wk. This may be given as a single dose or divided into daily injections such as 75 to 100 mg/m$^2$ on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m$^2$, 20 mg/m$^2$, 30 mg/m$^2$, 40 mg/m$^2$, 50 mg/m$^2$, 60 mg/m$^2$, 70 mg/m$^2$, 80 mg/m$^2$, 90 mg/m$^2$ or 100 mg/m$^2$. The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject Melphalan. Melphalan also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-(bis(2-chloroethyl)amino)-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of ~2.1.

Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3mg/kg/day or any dose in between these doses or above these doses. Some variation in dosage will necessarily occur depending on the condition of the subject being treated. The person responsible for administration will, in any event, determine the appropriate dose for the individual subject.

Cyclophosphamide. Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride (($ClCH_2CH_2$)$_2$N—$POCl_2$) in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug also sometimes is administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

Chlorambucil. Chlorambucil (also known as leukeran) is a bifunctional alkylating agent of the nitrogen mustard type that has been found active against selected human neoplastic diseases. Chlorambucil is known chemically as 4-(bis(2-chlorethyl)amino) benzenebutanoic acid.

Chlorambucil is available in tablet form for oral administration. It is rapidly and completely absorbed from the gastrointestinal tract. After single oral doses of 0.6-1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation.

Busulfan. Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

Lomustine. Lomustine is one of the nitrosoureas used in the treatment of certain neoplastic diseases. It is 1-(2-chloroethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are: magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m$^2$ to 100 mg/m$^2$, about half of the radioactivity given was excreted in the form of degradation products within 24 hours.

The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m$^2$ as a single oral dose every 6 wk. In individuals with compromised bone marrow function, the dose should be reduced to 100 mg/m$^2$ every 6 wk. When lomustine is used in combination with other myelosuppressive drugs, the doses should be adjusted accordingly. It is understood that other doses may be used for example, 20 mg/m$^2$ 30 mg/m$^2$, 40 mg/m$^2$, 50 mg/m$^2$, 60 mg/m$^2$, 70 mg/m$^2$, 80 mg/m$^2$, 90 mg/m$^2$, 100 mg/m$^2$, 120 mg/m$^2$ or any doses between these figures as determined by the clinician to be necessary for the individual being treated.

C. Radiotherapy

Radiotherapy, also called radiation therapy, involves the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly. Radiotherapy may be used to treat localized solid tumors, such as cancers of the skin, tongue, larynx, brain, breast, or cervix. It can also be used to treat leukemia and lymphoma (cancers of the blood-forming cells and lymphatic system, respectively). Certain radiation therapies have been used for nearly a century to treat human cancer (Hall, 2000).

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. For example, radiotherapy may be delivered at approximately 24-hr intervals at about 180-300 cGy/day. In certain instances, twice daily fractionation (about 110-160 cGy/day) may also be useful as a radiation therapy (Schulz, 2001; Crellin, 1993).

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets that are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of your internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques.

Stereotactic radiotherapy is used to treat brain tumors. This technique directs the radiotherapy from many different angles so that the dose going to the tumour is very high and the dose affecting surrounding healthy tissue is very low. Before treatment, several scans are analysed by computers to ensure that the radiotherapy is precisely targeted, and the patient's head is held still in a specially made frame while receiving radiotherapy. Several doses are given.

Stereotactic radio-surgery (gamma knife) for brain tumors does not use a knife, but very precisely targeted beams of gamma radiotherapy from hundreds of different angles. Only one session of radiotherapy, taking about four to five hours, is needed. For this treatment a patient will have a specially made metal frame attached to the patient's head. Then several scans and x-rays are carried out to find the precise area where the treatment is needed. During the radiotherapy, the patient lies with their head in a large helmet, which has hundreds of holes in it to allow the radiotherapy beams through.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia (i.e., the use of heat) is also being studied for its effectiveness in sensitizing tissue to radiation.

In certain embodiments of the present invention, the GSK3 inhibitor may be given before, during, or after a radiation therapy. The GSK3 inhibitor may precede or follow the radiation therapy by intervals ranging from minutes to weeks. In embodiments where the radiation therapy and the GSK3 inhibitor are applied separately to a cell, one would generally ensure that a significant period of time did not expire between the time of each delivery, such that the GSK3 inhibitor would still be able to exert a protective effect on the cell. For example, in such instances, it is contemplated that one may contact the cell, tissue or organism with two, three, four or more modalities substantially simultaneously (i.e., within less than about a minute) with the GSK3 inhibitor. In other aspects, a radiation therapy may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the GSK3 inhibitor. In certain other embodiments, a radiation therapy may be administered within from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the GSK3 inhibitor. In some situations, it may be desirable to extend the time period for treatment significantly, however, where several weeks (e.g., about 1, about 2, about 3, about 4, about 5, about 6, about 7 or about 8 weeks or more) lapse between the administration of the GSK3 inhibitor and the radiation therapy.

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, is may be desirable to use a radiation therapy to treat a hyperproliferative disease that is not cancer, such as a pre-cancerous disease (e.g., a pre-cancerous tumor), or a non-cancerous disease (e.g., a benign tumor). The hyperproliferative disease may be a benign tumor, such as a benign tumor of the brain, spinal cord, eye, or lung. Additional diseases which can be treated with a radiation therapy and could benefit from the present invention include: arterovenous malformations, neuromas (e.g., acoustic neuromas, optic neuromas), meningiomas, schwanomas, adenomas (e.g., a pituitary adenoma), and gliomas (e.g., optic gliomas).

Central nervous system (CNS) and peripheral nervous system (PNS) neurons, nerves, and/or regions can be damaged by radiation therapy. It is specifically envisioned that the present invention may be used to protect one or more region of the CNS and/or PNS. For example, the spinal cord, optic nerve, brachial plexus, sacral nerves, and/or sciatic nerve may be damaged by a radiation therapy. Thus, in certain embodiments of the present invention, one or more of the spinal cord, optic nerve, brachial plexus, sacral nerves, and/or sciatic nerve is protected partially or completely from a radiation therapy by administering a GSK3 inhibitor in combination with the radiation therapy.

Radiation therapies can also damage other non-neuronal tissues including tissues of the endothelium and/or vasculature (e.g., tissues comprising blood vessels), salivary glands, GI tract, lung, and/or liver. In certain embodiments of the present invention, a GSK3 inhibitor may be used to reduce or prevent damage from a radiation therapy to tissue of one or more non-neuronal tissue, such as a tissue of the endothelium or vasculature (e.g., tissues comprising blood vessels), salivary glands, GI tract, lung, or liver.

D. Surgery

Approximately 60% of persons with cancer will undergo surgery of some type, which includes, for example, preventative, diagnostic or staging, curative and palliative surgery. Surgery, and in particular a curative surgery, may be used in conjunction with other therapies, such as the present invention and one or more other agents.

Curative surgery includes resection in which all or part of cancerous tissue is physically removed, excised and/or destroyed. It is further contemplated that surgery may remove, excise or destroy superficial cancers, precancers, or incidental amounts of normal tissue. Treatment by surgery includes for example, tumor resection, laser surgery, cryosurgery, electrosurgery, and microscopically controlled surgery (Mohs' surgery). Tumor resection refers to physical removal of at least part of a tumor. Upon excision of part of all of cancerous cells, tissue, or tumor, a cavity may be formed in the body.

Further treatment of the tumor or area of surgery may be accomplished by perfusion, direct injection or local application of the area with an additional anti-cancer agent, such as chemo- or radiotherapy. Such treatment may be repeated, for example, about every 1, about every 2, about every 3, about every 4, about every 5, about every 6, or about every 7 days, or about every 1, about every 2, about every 3, about every 4, or about every 5 weeks or about every 1, about every 2, about every 3, about every 4, about every 5, about every 6, about every 7, about every 8, about every 9, about every 10, about every 11, or about every 12 months. These treatments may be of varying dosages as well.

VII. Pharmaceutical Formulations and Routes of Administration

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Supplementary active ingredients also can be incorporated into the compositions.

Administration of these compositions according to the present invention will be via any common route so long as the target tissue is available via that route. This includes intradermal, subcutaneous, intramuscular, intraperitoneal or intravenous injection. In particular, intratumoral routes and sites local and regional to tumors are contemplated. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy administration by a syringe is possible. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

For oral administration the polypeptides of the present invention may be incorporated with excipients that may include water, binders, abrasives, flavoring agents, foaming agents, and humectants.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Patients. Stanford investigators conducted the original phase I and phase II clinical trials of Rituximab. During the course of those studies, they collected tumor biopsy specimens for all patients prior to receiving the antibody. In addition, they conducted a trial of re-treatment of patients who had originally responded to Rituximab and then relapsed. They continued to follow all the patients, especially those who have had long-term remissions. Since the approval of Rituximab, they continued to acquire pre-treatment biopsy specimens on patients prior to their treatment and to record clinical outcomes. From their database we had access to genomic DNA samples and clinical records from 85 subjects with follicular lymphoma and anti-CD20 therapy. Thus far we processed and analyzed 70 patients. All specimens were coded and processed for C1qA polymorphisms at the University of Iowa in a blinded fashion. In addition to the specimens received from Stanford, approximately 35 patients from UIHC and Mayo will be selected upon verifying the availability of peripheral blood or genomic DNA samples and and records on the clinical response to Rituximab. The pathology of all subjects will be reviewed. Subjects with follicular small cleaved, follicular large cell and follicular mixed lymphoma will be included. A prerequisite for inclusion in this study is that the subject did not receive chemotherapy within the two months prior to initiation of the Rituximab therapy.

Assessment of clinical response to Rituxan therapy. Clinical responses are determined by physical examination, computed tomography scanning and pathology (for bone marrow) between 1 and 3 months after last rituximab administration, and every 3 months thereafter. The clinical response is scored according to the Cheson criteria (Cheson et al., 1999). Cheson criteria employs data obtained mainly from physical examination and computed tomography scans to determine clinical response to therapy of NHL. Thus, a complete response (CR) requires: complete disappearance of all detectable clinical and radiographic evidence of disease and disappearance of all disease-related symptoms if present before therapy, normalization of biochemical abnormalities, all lymph nodes and nodal masses must have regressed to normal size, return of spleen size to normal if enlarged before therapy, and clearance of bone-marrow infiltrate. The unconfirmed complete response (CRu) is defined as fulfilling the physical examination and radiographic criteria of the complete response but with residual lymph node masses greater than 1.5 cm after total reduction of at least 75% due to therapy and/or indeterminate bone marrow. Partial response (PR) requires more than 50% decrease in the sum of all products of the greatest diameters (SPD) of the six largest dominant nodes or nodal masses, no increase in the size of other nodes, liver or spleen, splenic and hepatic nodules must decrease by at least 50% in the SPD, no measurable disease involving other organs, and no new sites of disease. Relapsed disease requires appearance of any new lesion or increase by more than 50% in the size of previously involved sites. Progressive disease requires more than 50% increase from nadir in the SPD of any previously identified abnormal node and appearance of any new lesion during or at the end of therapy. Finally, stable disease is defined as less than partial response but absence of progressive disease.

PCR™ Restriction Fragment-Length Polymorphism Analysis. For the PCR™ amplification of the whole C1qA gene the following primers were used: forward 5'TGAGTGT-GTGAAGATGTGGG (SEQ ID NO:1) and reverse 5'AGGG-TAGTGGTTAAACACAGG (SEQ ID NO:2). A first denaturation step at 94° C. for 3 min was followed by 35 cycles of denaturation at 94° C. 20 sec, annealing at 58° C. for 30 sec, extension at 68° C. for 3 min, and a 10 min final extension step. To ensure accuracy of sequencing data, Platinum Taq High-Fidelity (Invitrogen) was the enzyme of choice. The PCR™ product was extracted from 1% agarose gels using fiberglass columns and used for direct sequencing. For RFLP analysis, the target template containing the $C1qA_{[276}A/G]$ polymorphism was amplified using forward 5'TAAAG-GAGACCAGGGGGAAC (SEQ ID NO:3) and reverse 5'TTGAGGAGGAGACGATGGAC (SEQ ID NO:4) primers with an extension step reduced to 45 seconds. Prior to restriction digest, the amplicons were purified by extraction with phenol-chloroform and precipitation with ethanol.

Enzymatic digestion with ApaI restriction endonuclease (New England Biolabs, Beverly, Mass.) was used to analyze the $C1qA_{[276]}$ polymorphism. Enzymatic digestion with ApaI of the 338 base PCR™ product containing the $C1qA_{[276G]}$ allelic sequence results in 4 fragments of variable length from 7 bp to 269 bp. The largest of these fragments can be visualized on agarose gels. $C1qA_{[276A]}$ allele lacks the third Apa I restriction site (GGGCC/C) at the codons for Gly92 (GGG) and Ala93 (GCC), and thus yields a heavier fragment of 288 bp after ApaI digestion. Separation of restriction digest fragments was done in 2.5% agarose gels FIG. 1. Results obtained from the RFLP analysis were confirmed by DNA sequencing using the dye terminator cycle sequencing method with AmpliTaq DNA polymerase and FS enzyme (PE Applied Biosystems, Foster City, Calif.) and forward 5'GAGTCT-CATGGAATCAC (SEQ ID NO:5) sequencing primer. The reactions were run and analyzed with Applied Biosystems Model 373A stretch fluorescent automated sequencer at the University of Iowa DNA Core Laboratory Facility.

Example 2

Results

Figure 2:
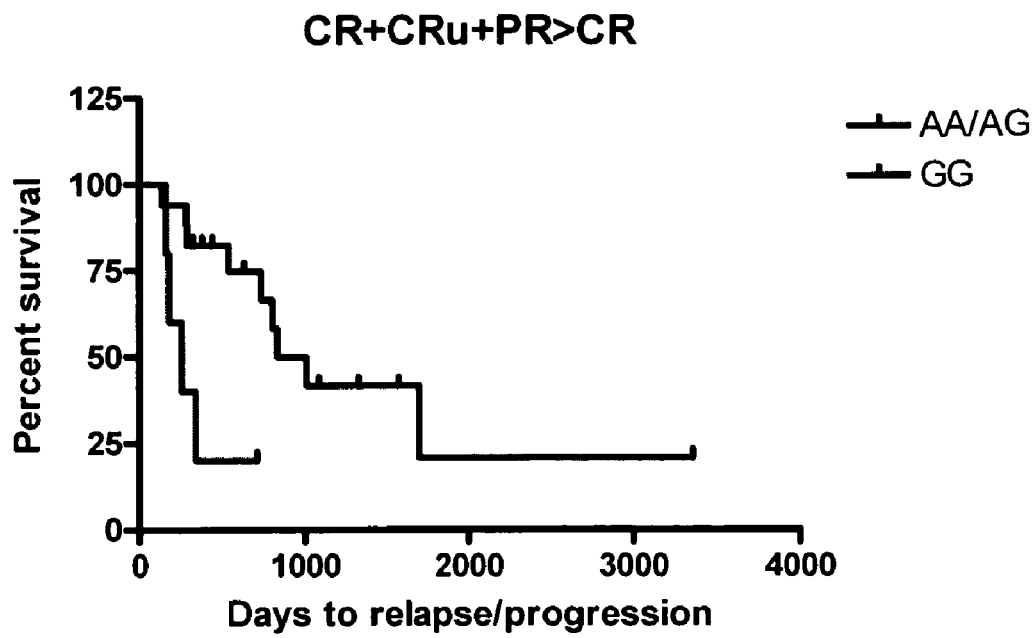
FIG. 2—AA/AG vs GG at C1qA276. Comparison of Survival Curves in patients that reached complete remission after Rituximab. Logrank Test: Chi square=7.142, df=1, P value=0.0075. Median survival: Data 1:AA/AG=830.0 days; Data 1:GG=250.0 days; Ratio=3.320, 95% CI of ratio=3.012 to 3.628. Hazard Ratio: Ratio=0.2433, 95% CI of ratio=0.01075 to 0.4980. Note: homozygous G patients are at least 4× more likely to lose complete remission sooner than AA/AG patients.
Figure 3:
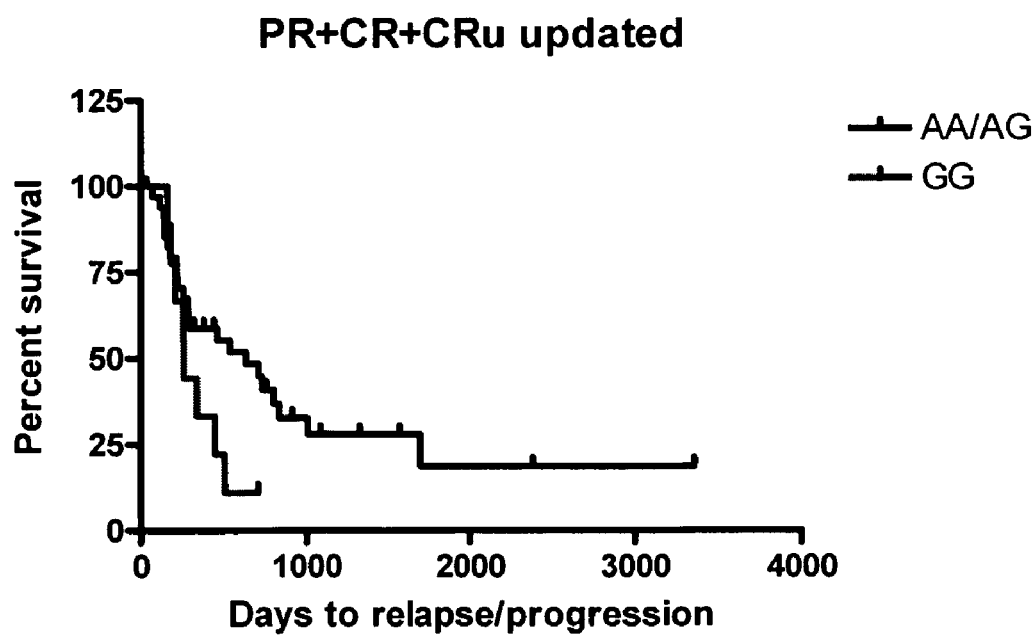
FIG. 3—AA/AG vs GG at C1qA276. Comparison of Survival Curves in all patients who responded to Rituximab (excludes non-responders only). Logrank Test: Chi square=3.448, df=1, P value=0.0633. Median survival: Data 1:AA/AG=627.0 days; Data 1:GG=255.0 days; Ratio=2.459; 95% CI of ratio=2.012 to 2.906. Hazard Ratio: Ratio=0.4850; 95% CI of ratio=0.1339 to 1.056.

The logrank test/Chi square on the clinical data received from Stanford (with clinical follow-up well beyond the first year after therapy) are shown below FIG. 2. If one considers only the patients in CR and CRu status, there is a strong association between the A allele and better/prolonged remission after Rituximab therapy (we used days from the end of therapy to relapse/progression of disease). P value is highly significant (p=0.0075). It appears that the homozygous GG subjects are at least 4× more likely to relapse than AA/AG subjects (HR 4.11, 95% CI=2.0 to 93.0). Sample size is: AA=6, AG=11, GG=5. If one considers all patients that showed a response to Rituximab (that is PR, CR and CRu combined), the p value is approaching significance (p=0.063) and may become significant if the sample size is increased (current sample size: AA=13, AG=23, GG=9). Although the sample size is rather small, at this point there appears to be an association between the A allele and prolonged disease free survival after Rituximab therapy. The total number of subjects entered into this study is expected to increase to 105-110 over the following three weeks. The results obtained so far agree with previous observations in breast cancer and metastasis where the A allele (especially the AA homozygous genotype) appeared to protect against spread of tumor.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

IX. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,683,195
U.S. Pat. No. 4,683,202
U.S. Pat. No. 4,800,159
U.S. Pat. No. 4,883,750
U.S. Pat. No. 5,242,974
U.S. Pat. No. 5,279,721
U.S. Pat. No. 5,384,261
U.S. Pat. No. 5,405,783
U.S. Pat. No. 5,412,087
U.S. Pat. No. 5,424,186
U.S. Pat. No. 5,429,807
U.S. Pat. No. 5,436,327
U.S. Pat. No. 5,445,934
U.S. Pat. No. 5,472,672
U.S. Pat. No. 5,527,681
U.S. Pat. No. 5,529,756
U.S. Pat. No. 5,532,128
U.S. Pat. No. 5,545,531
U.S. Pat. No. 5,554,501
U.S. Pat. No. 5,556,752
U.S. Pat. No. 5,561,071
U.S. Pat. No. 5,571,639
U.S. Pat. No. 5,593,839
U.S. Pat. No. 5,599,695
U.S. Pat. No. 5,624,711
U.S. Pat. No. 5,658,734
U.S. Pat. No. 5,700,637
U.S. Pat. No. 5,757,994
U.S. Pat. No. 5,788,166
U.S. Pat. No. 5,838,002
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709

U.S. Pat. No. 5,846,710
U.S. Pat. No. 5,846,717
U.S. Pat. No. 5,846,726
U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Pat. No. 5,986,258
U.S. Pat. No. 6,004,755
U.S. Pat. No. 6,585,739
U.S. Pat. No. RE 35,413
Abbondanzo, *Ann. Diagn. Pathol.*, 3(5):318-327, 1999.
Allred et al., *Breast Cancer Res. Treat.*, 16:182(149), 1990.
Anderson et al., *Blood*, 63(6):1424-1433, 1985.
Antibodies: A Laboratory Manual, Cold Spring Harbor Laboratory, Cold Spring Harbor Press, Cold Spring Harbor, N.Y., 1988.
Bahret al., *J. Mass Spectrom.*, 32:1111-1116, 1997.
Baldwin et al., *Transplantation*, 67(11):1498-1499, 1999.
Bentzley et al., *Anal Chem.*, 68(13):2141-2146, 1996.
Brown et al. *Immunol. Ser.*, 53:69-82, 1990.
Bucknall et al., *J. Am. Soc. Mass Spectrom.*, 13(9):1015-1027, 2002.
Caprioli et al., *Anal. Chem.*, 69:4751, 1997.
Caragine et al., *Blood*, 100(9):3304-3310, 2002a.
Caragine et al., *Cancer Res.*, 62(4):1110-1115, 2002b.
Carlini et al., *Genetics*, 159(2):623-633, 2001.
Chamberlan et al., In: *PCR Protocols*, Innis et al. (Eds.), Academic Press, NY, 272-281, 1990.
Chaurand et al., *Anal Chem.*, 71(23):5263-5270, 1999.
Chen et al., *Nat. Biotechnol.*, 19:537-542, 2001.
Cheson et al., et al., *J. Clin. Oncol.*, 17(4):1244, 1999.
Crellin et al., *Clin. Oncol.*, 5:5139-142, 1993.
De Jager et al., *Semin. Nucl. Med*, 23(2):165-179, 1993.
Demidem et al., *Cancer Biother. Radiopharm.*, 12(3):177-186, 1997.
Desiderio et al., *J. Mass Spectrom.*, 35(6):725-733, 2000.
Desiderio et al., *Methods Mol. Biol.*, 61:57-65, 1996.
Donin et al., *Clin. Exp. Immunol.*, 131(2):254-263, 2003.
Doolittle and Ben-Zeev, *Methods Mol Biol*, 109:215-237, 1999.
Duan et al., *Hum. Mol. Genet.*, 12(3):205-216, 2003.
Duncan et al., *Rapid Commun. Mass Spectrom.*, 7(12):1090-1094, 1993.
Eccles, *Breast Cancer Res.*, 3(2):86-90, 2001.
Einfeld et al., *EMBO J.*, 7(3):711-717, 1988.
Emmert et al., *Nucleic Acids Res.*, 29(7):1443-1452, 2001.
European Pat. 0 364 255
European Pat. 320 308
European Pat. 329 822
Faulstich et al., *Anal. Chem.*, 69(21):4349-4353, 1997.
Fenn et al., *Science*, 246(4926):64-71, 1989.
Fishelson et al., *Mol. Immunol.*, 40(2-4):109-123, 2003.
Frohman, *PCR Protocols. A Guide To Methods And Applications*, Academic Press, New York, 1990.
GB Appln. 2 202 328
Gelderman et al., *Trends Immunol.*, 25(3):158-164, 2004.
Gobom et al., *Anal. Chem.*, 72(14):3320-3326, 2000.
Golay et al., *Blood*, 95(12):3900-3908, 2000.
Gorter and Meri, *Immunol. Today*, 20(12):576-582, 1999.
Gulbis and Galand, *Hum. Pathol.*, 24(12):1271-1285, 1993.
Hakulinen and Meri, *Am. J. Pathol.*, 153(3):845-855, 1998.
Hall, In: *Radiobiology for Radiologist*, 5$^{th}$ Ed., Lippincott Williams and Wilkins, Philadelphia, 5-17, 2000.
Harjunpaa et al., *Scand. J. Immunol.*, 51(6):634-641, 2000.
Horak et al., *Rapid Commun. Mass Spectrom.*, 15(4):241-248, 2001.
Innis et al., *Proc. Natl. Acad. Sci. USA*, 85(24):9436-9440, 1988.
Jespersen et al., *Anal. Chem.*, 71(3):660-666, 1999.
Jiang et al., *Biochem. Pharmacol.*, 59:763-772, 2000.
Jurianz et al., *Immunopharmacology*, 42(1-3):209-18, 1999.
Kabarle et al., *Anal. Chem.* 65(20):972A-986A, 1993.
Kanazawa et al., *Biol. Pharm. Bull.*, 22(4):339-346, 1999.
Kazmaier et al., *Anesthesiology*, 89(4):831-817, 1998.
Khan et al., *Nucleic Acids Res.*, 30(16):3624-3631, 2002.
Kwoh et al., *Proc. Natl. Acad. Sci. USA*, 86:1173, 1989.
Li et al., *Trends Biotechnol.*, 18:151, 2000.
Lovelace et al., *J. Chromatogr.*, 562(1-2):573-584, 1991.
Lynn et al., *J. Mol. Evol.*, 48(5):605-614, 1999.
Marie et al., *Anal. Chem.*, 72(20):5106-5114, 2000
Miketova et al., *Mol. Biotechnol.*, 8(3):249-253, 1997
Mirgorodskaya et al., *Rapid Commun. Mass Spectrom.*, 14(14):1226-1232, 2000,
Modrek et al., *Nucleic Acids Res.*, 29(13):2850-2859, 2001.
Muddiman et al., *Fres. J Anal. Chem.*, 354:103, 1996.
Mueller and Wold, *Science* 246, 780-786, 1989.
Nakamura et al., In: *Handbook of Experimental Immunology* (4$^{th}$ Ed.), Weir et al. (Eds), 1:27, Blackwell Scientific Publ., Oxford, 1987.
Nelson et al., *Anal. Chem.*, 66:1408, 1994.
Nguyen et al., *J. Chromatogr. A.*, 705(1):21-45, 1995.
Ohara et al., *Proc. Natl. Acad. Sci.* USA, 86:5673-5677, 1989.
Onoe et al., *Immunobiology*, 206(4):377-391, 2002.

PCT Appln. PCT/US87/00880
PCT Appln. PCT/US89/01025
PCT Appln. WO 88/10315
PCT Appln. WO 89/06700
PCT Appln. WO 90/07641
Press et al., *Blood,* 69(2):584-591, 1987.
Racila et al., *J. Exp. Med.,* 181(4):1539-1550, 1995.
Racila et al., *Lupus,* 12(2):124-132, 2003.
Reff et al., *Blood,* 83(2):435-445, 1994.
Remington's Pharmaceutical Sciences, 15$^{th}$ ed., 33:624-652, Mack Publishing Company, Easton, Pa., 1980.
Roepstorff, *EXS.* 2000;88:81-97, 2000.
Sambrook et al., In: *Molecular cloning,* Cold Spring Harbor Laboratory Press, Cold Spring Harbor, N.Y., 1989.
Sanger et al., *Proc. Natl. Acad. Sci. USA,* 74:5463-5467, 1977.
Sanger, *Annu. Rev. Biochem.,* 57:1-28, 1988.
Schulz et al., *Curr. Oncol. Rep.,* 3:179-184, 2001.
Smith and Rutledge, *Natl. Cancer Inst. Monogr.,* 42:141-143, 1975.
Stoeckli et al., *Nat. Med.,* 7(4):493-496, 2001.
Takach et al., *J. Protein Chem.,* 16:363, 1997.
Tazawa et al., *Am. J. Pathol.,* 163(6):2221-2232, 2003.
Tedder et al., *J. Cell Biochem.,* 14D:195, 1990.
Tedder et al., *J. Immunol.,* 135(2):973-979, 1985.
Valentine et al., *J. Biol. Chem.,* 264(19):11282-11287, 1989.
Villanueva et al., *Enzyme Microb. Technol.,* 29:99, 1999.
von Ahsen et al., *Blood,* 103(2):586-593, 2004.
Walker et al., *Nucleic Acids Res.,* 20(7):1691-1696, 1992.
Wang et al., *Anal. Chem.,* 72(21):5285-5289, 2000.
Wang et al., *Br. J. Cancer,* 80:1617-1622, 1999.
Webb et al., *Exp. Hematol.,* 31(6):488-494, 2003.
Wittmann et al., *Biotechnol. Bioeng.,* 72:642, 2001.
Wu et al., *Anal. Chem.,* 70:456A, 1998.
Wu et al., *Biochim. Biophys. Acta,* 1466:315-327, 2000.
Yang et al., *J. Biol. Chem.,* 275:26892-36898, 2000.
Young et al., *N Engl J Med.* 7:299(23):1261-1266, 1978.
Zhong et al., *Clin. Chem. ACTA.,* 313:147, 2001.
Zweigenbaum et al., *Anal. Chem.,* 71(13):2294-300, 1999.
Zweigenbaum et al., *J. Pharm. Biomed. Anal.,* 23(4):723-733, 2000.

What is claimed is:

1. A method for determine an increased likelihood that a human subject will have a prolonged response period to treatment of follicular lymphoma with Rituximab monoclonal antibody therapy, said method comprising:
   (a) obtaining a sample from said subject, said sample comprising nucleic acids from the subject;
   (b) detecting in said nucleic acids the presence of at least one allele of the ClqA gene comprising an A nucleotide at the position corresponding to position 276 of SEQ ID NO:6; and
   (c) correlating the presence of said A nucleotide with an increased likelihood that the subject will have a prolonged response period to treatment of follicular lymphoma with Rituximab monoclonal antibody therapy.

2. The method of claim 1, wherein detecting comprises sequencing, primer extension, differential hybridization, RFLP analysis, SNP analysis, molecular beacon analysis, and mass spectrometry.

3. The method of claim 2, wherein detecting comprises PCR-based sequencing.

4. The method of claim 1, further comprising obtaining genomic DNA from said subject.

5. The method of claim 1, wherein said patient has not been previously diagnosed with cancer.

6. The method of claim 1, wherein said patient has been previously diagnosed with cancer.

7. The method of claim 1, wherein said patient has previously been treated with an anti-CD20 antibody.

8. The method of claim 1, wherein said patient has not been treated with an anti-CD20 antibody.

9. The method of claim 1, further comprising making a treatment decision based on step (c).

10. The method of claim 1, further comprising treating said patient.

11. The method of claim 10, wherein treating comprises treating with Rituximab monoclonal antibody therapy.

12. The method of claim 10, wherein treating comprises surgery, chemotherapy, radiotherapy, hormonal therapy, immunotherapy other than rituximab, cytokine therapy or gene therapy.

* * * * *

UNITED STATES PATENT AND TRADEMARK OFFICE
CERTIFICATE OF CORRECTION

PATENT NO.         : 7,723,036 B2
APPLICATION NO.    : 11/505635
DATED              : May 25, 2010
INVENTOR(S)        : Emilian V. Racila et al.

Page 1 of 1

It is certified that error appears in the above-identified patent and that said Letters Patent is hereby corrected as shown below:

In claim 1, column 47, line 10, delete "determine" and insert --determining-- therefor.

Signed and Sealed this

Twenty-fourth Day of August, 2010

David J. Kappos
*Director of the United States Patent and Trademark Office*